United States Patent
Papakonstantinou et al.

(10) Patent No.: US 9,406,037 B1
(45) Date of Patent: Aug. 2, 2016

(54) INTERACTIVE LITERATURE ANALYSIS AND REPORTING

(71) Applicant: BioHeatMap, Inc., La Jolla, CA (US)

(72) Inventors: Yannis Papakonstantinou, La Jolla, CA (US); Robert Meadows, San Diego, CA (US)

(73) Assignee: BioHeatMap, Inc.

( * ) Notice: Subject to any disclaimer, the term of this patent is extended or adjusted under 35 U.S.C. 154(b) by 128 days.

(21) Appl. No.: 13/657,810

(22) Filed: Oct. 22, 2012

Related U.S. Application Data

(60) Provisional application No. 61/549,679, filed on Oct. 20, 2011.

(51) Int. Cl.
G06Q 10/06 (2012.01)
(52) U.S. Cl.
CPC .................... G06Q 10/063 (2013.01)
(58) Field of Classification Search
None
See application file for complete search history.

(56) References Cited

U.S. PATENT DOCUMENTS

| | | | |
|---|---|---|---|
| 2002/0169762 A1 | 11/2002 | Cardona | |
| 2004/0103090 A1 | 5/2004 | Dogl et al. | |
| 2006/0074836 A1* | 4/2006 | Gardner et al. | 706/60 |
| 2006/0235843 A1 | 10/2006 | Musgrove et al. | |
| 2007/0011183 A1* | 1/2007 | Langseth et al. | 707/101 |
| 2008/0082495 A1* | 4/2008 | Polo-Malouvier et al. | 707/3 |
| 2008/0243778 A1* | 10/2008 | Behnen et al. | 707/3 |
| 2009/0112835 A1* | 4/2009 | Elder | 707/4 |
| 2010/0198778 A1* | 8/2010 | Venugopal et al. | 707/602 |
| 2011/0060769 A1* | 3/2011 | Mohan | 707/803 |
| 2011/0093449 A1 | 4/2011 | Belenzon et al. | |
| 2011/0137705 A1* | 6/2011 | Srinivasan | 705/7.28 |
| 2011/0169835 A1* | 7/2011 | Cardno et al. | 345/440 |
| 2011/0258167 A1* | 10/2011 | Binstock et al. | 707/690 |
| 2012/0005228 A1* | 1/2012 | Singh | 707/769 |
| 2012/0096142 A1* | 4/2012 | Suit | 709/224 |

FOREIGN PATENT DOCUMENTS

EP 1739584 A1 1/2007

* cited by examiner

*Primary Examiner* — Tarek Chbouki
(74) *Attorney, Agent, or Firm* — Perkins Coie LLP

(57) ABSTRACT

Techniques for performing searches and presenting reports to users include receiving a user query request comprising condition classifications or text words or text phrases, receiving a user report request comprising report classification information that includes a request term, accessing an ontology providing a plurality of classifications, where each classification comprises a set of terms, accessing, using the ontology, a set of document associated with the report classification information, computing an aggregate measure of the request term based on a relationship between the request term and the set of documents, generating a requested report based on the aggregate measure of the request term and presenting the requested report.

20 Claims, 13 Drawing Sheets

FIG. 7

INTERACTIVE LITERATURE ANALYSIS AND REPORTING

CROSS-REFERENCE TO RELATED APPLICATIONS

The present document claims the benefit of priority under 35 USC §119(e) from U.S. Provisional Patent Application 61/549,679, titled "EFFICIENT INTERACTIVE LITERATURE ANALYSIS," filed on Oct. 20, 2011. The aforementioned provisional patent application document is incorporated by reference in the present document in its entirety.

FEDERALLY SPONSORED RESEARCH OR DEVELOPMENT

The research and development for the subject matter described in this document received funding under Grant No. 1114059 from the National Science Foundation Small Business Innovation Research program. The government has certain rights in the invention.

BACKGROUND

With recent progress in computer connectivity, e.g., the Internet and the World Wide Web, it is now possible for users to search databases and electronic documents for information using computers. Users may query computers and servers that are physically located far away, such as another country or another continent. Often, a user's search may result in hundreds or thousands of search results, which may overwhelm the user.

SUMMARY

This document describes a web application that in coordination with one or more databases allows users to search and analyze aspects of a literature utilizing multiple classifications of ontology data. The present document discloses a novel ability to provide to the user aggregate measures about various terms that appear in the literature of interest—as opposed to merely providing a result set of documents.

Certain aspects of the disclosed techniques, as applied to the biomedical space, are used to provide example implementations and uses. However, the application to the biomedical space is only for illustrative purposes and does not limit the scope of the disclosed techniques. Some embodiments discussed in this document are collectively called BioHeatMap in the rest of this document. BioHeatMap can be used, e.g., by researchers and decision making executives working on drug discovery, either in pharmaceutical companies or in academic organizations.

The document describes the implementation of functionalities for analyzing a literature body (e.g., biomedical literature) that may come from one or more information sources. The teachings of this document enable a system that allows its users to efficiently analyze a vast literature according to ontology terms that have been discovered in the ontology. In the case of biomedical literature, such analysis serves, without limitation, the purpose of detecting emerging, promising connections between candidate active substances (drugs), clinical indications (diseases), molecular targets and other entities of interest to the pharmaceutical researcher working on drug discovery. BioHeatMap enables its users to easily link their findings to academic experts, patents, FDA filings and other data pertaining to the discovered connections. This includes a la carte access to articles and data of for-pay information sources. BioHeatMap's development relies on the teachings of this document on entity resolution, on-line analytical processing, controlled crowdsourcing and semi-structured data search.

Further examples of the types of discovery that a user can achieve with BioHeatMap are:

Novel findings for existing active substances (i.e., drugs) of the pharmaceutical company, which may lead to new prescription opportunities for the existing drug portfolio. For example, the heatmap visualization of FIG. 1 shows which indications are connected with substances in the vasopressin family. By clicking on a number the researcher sees multiple navigation options. One option allows the user to review the titles of the papers that connect the respective substance and indication and can proceed to browse them. Another option allows the user to see how these papers categorize in other classifications. In this document, the term "classifications" is also referred to as "dimensions" in the report visualization. For example, FIG. 1 shows a visualization where the vertical dimension/classification is "substances" and the horizontal dimension/classification is "diseases." In a navigation example, a navigation option could bring up a bar chart that shows when the papers used for formulating a correlation were published year-by-year.

In yet another example, the researcher may discover novel active substances and respective findings in the therapeutic areas that the company focuses.

The details of one or more implementations are set forth in the accompanying attachments, the drawings, and the description below. Other features will be apparent from the description and drawings.

BRIEF DESCRIPTION OF THE DRAWINGS

FIG. 7 shows an example of query formulating interface and a heatmap relating substances with diseases/indications.

DETAILED DESCRIPTION

Figure 1:
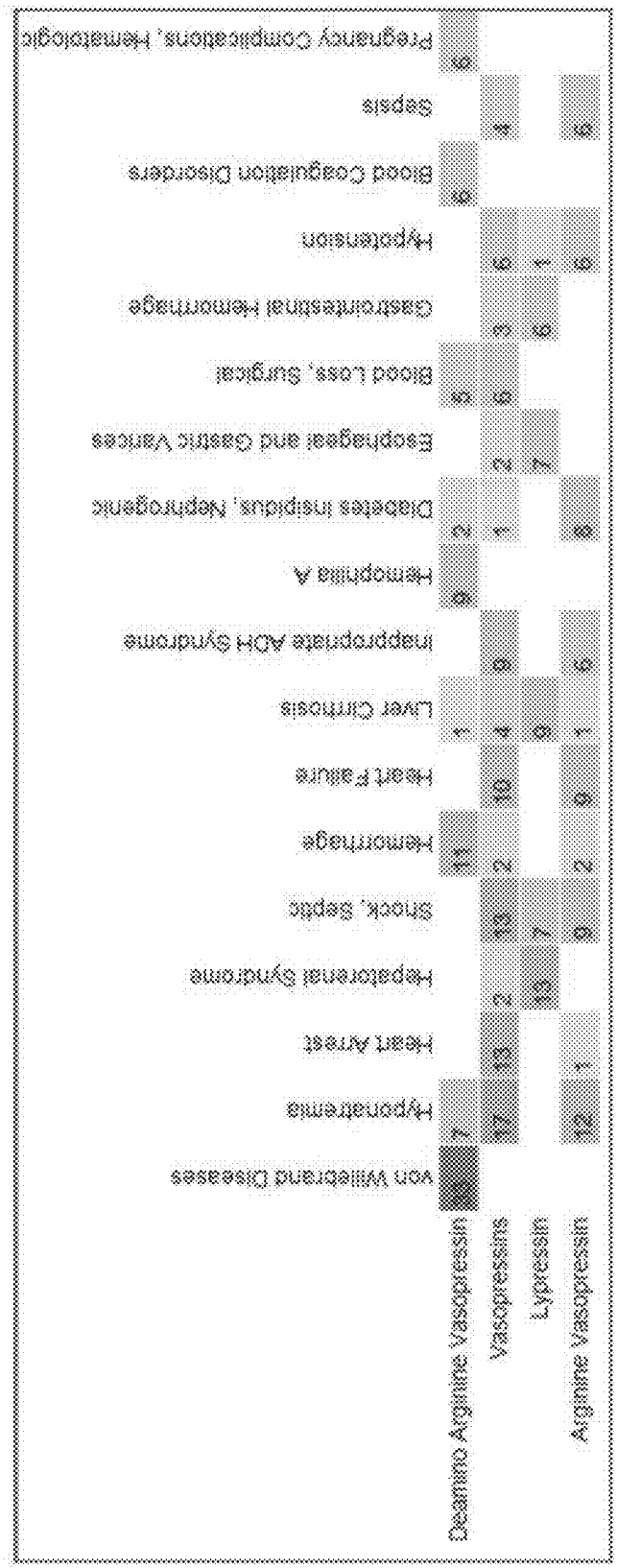
FIG. 1 shows an example heatmap analyzing literature across two dimensions, substance and disease.

The present document relates to database and documents containing computer readable data. More particularly, it concerns a computer implemented system to assist users to analyze aspects of a literature and search the literature utilizing an ontology.

The typical operation of a prior art search engine can be summarized as follows: The user submits (typically via a web browser application) a keyword search, i.e., a search that consists of a set of words or even phrases. In response, the search engine returns an ordered set of documents, where the ordering is according to the relevance of a document to the search. In the case of web search, the documents are web pages.

Multiple improvements and additional features exist over the basic search model: For example, the user may be able to specify more complex requests where he specifies that certain words or phrases are within a certain distance. More commonly, even if the user has not specified explicitly such complex requests, the search engine may have already included in its default settings criteria (such as the distance of the request's words) that affect the ranking accordingly. Generally, aggressive introduction of common default options is prevalent in the prior art and can also be used with the techniques disclosed in the present document.

Furthermore, some existing services, such as the government funded PubMed search engine include a limited use of ontologies to improve the quality of search. The PubMed search engine of the biomedical literature employs the MeSH ontology, which classifies substances, diseases and other terms of importance to biomedical researchers. Interestingly, many classifications (e.g., the substance classification, the disease classification, etc.) have a term/subterm structure of arbitrary depth. For example, the term "deamino arginine vasopressin" is a subterm of "arginine vasopressin", which is a subterm of "vasopressin", which is a subterm of "neuropeptides", which is a subterm of "peptides", etc. Generally a term may be a subterm of multiple parent terms. Terms generally have multiple synonyms. For example, "deamino arginine vasopressin" is also known as "desmopressin" and is also known with various pharmaceutical brand names. Certain embodiments disclosed in the present document could use the MeSH ontology. Ontologies improve the recall and therefore the overall quality of the search.

Referring back to the PubMed search engine, a user may ask PubMed for articles about "desmopressin". In response to this request, PubMed could rewrite the query to also find articles that involve the synonym "deamino arginine vasopressin". In yet another example, when a search for a term is issued on a system utilizing a term/subterm ontology, the system may elect to also look for documents that involve subterms of the requested term. For example, when the user requests documents involving "vasopressin", the returned list of documents may also include a document that involves "desmopressin", which is a subterm of "vasopressins".

However, the current search engine functionalities are inadequate when the return consists of multiple documents, which the user has to read in order to understand correlations between various terms. For example, consider a pharmaceutical researcher interested in the following questions about vasopressins: Which particular vasopressin subterms have been associated with particular diseases, according to the literature? Who are the leading authors with each vasopressins/disease association? The current state of the search art makes often practically impossible to obtain answers to such questions. For example, consider the researcher interested in diseases associated to the vasopressin category: The researcher will ask for vasopressins documents at PubMed. As of the filing of this document, there are about 32,000 qualifying articles. Then the researcher may need to create a massive disease/substance spreadsheet, open each of the 32,000 articles and read it to spot which disease/substance combinations each article talks about.

Further complicating the problem and revealing further inadequacies of current systems is questions such as: What are the important emerging associations between vasopressins and diseases? In the latter question, a useful (to the biomedical researcher) notion of "emerging association" is that the number of recent articles on a substance/disease association has broken above its historical average. Similarly, a concept of "important" may need to take into account the business semantics of a particular business domain. For example, a clinical trial will likely matter more to the pharmaceutical researcher investigating substance/disease connections. Such "business importance" metrics must be appropriately accounted for in the aggregates. Techniques, further disclosed below, address the above-discussed and other limitations with present day search engines. In addition, the search results to a user query are presented in a visually informative display, such as a two dimensional graph, that visualizing aggregates answers that a user is looking for. In the description below, section headers are used only for improving readability of the disclosed subject matter and do not in any way limit the scope of the claimed subject matter.

System Architecture

The following description provides a high level architecture. BioHeatMap accesses the sources depicted in FIG. 2, which may be public or for-pay. Some sources provide articles, including data that describe various findings. For example, PubMed provides articles and citations of research papers, case studies and clinical trials; USPTO provides patents; and so on. For the sake of the following discussion they are all called articles.

Other sources offer metadata terms, which include terminologies, classifications, ontologies, and identification systems. The metadata terms are generally used in articles. The same web application may provide both articles and metadata terms. For example, PubMed offers the MeSH ontology, which is an important metadata source for BioHeatMap. MeSH includes a hierarchical classification of indications/diseases (recall, however, that MeSH is not the only source of disease names), substances and more. PubMed's articles are annotated (typically within a few months after their publication) with MeSH terms, i.e., they are annotated with indications and substances.

For integration purposes, especially important sources are those (such as, DrugBank) that connect the metadata terms of multiple sources, by providing the correspondence between the multiple identities of an entity in different sources or by providing relationships between entities. A prominent example is Wikipedia, where many articles about substances provide semi structured tables that relate the Chemical Abstracts Service identity of the substance with the substance's INN, with its MeSH term. Also important for integration are the curated data on identities and relationships, provided by the users, which also become part of BioHeatMap's datamart.

Figure 2:
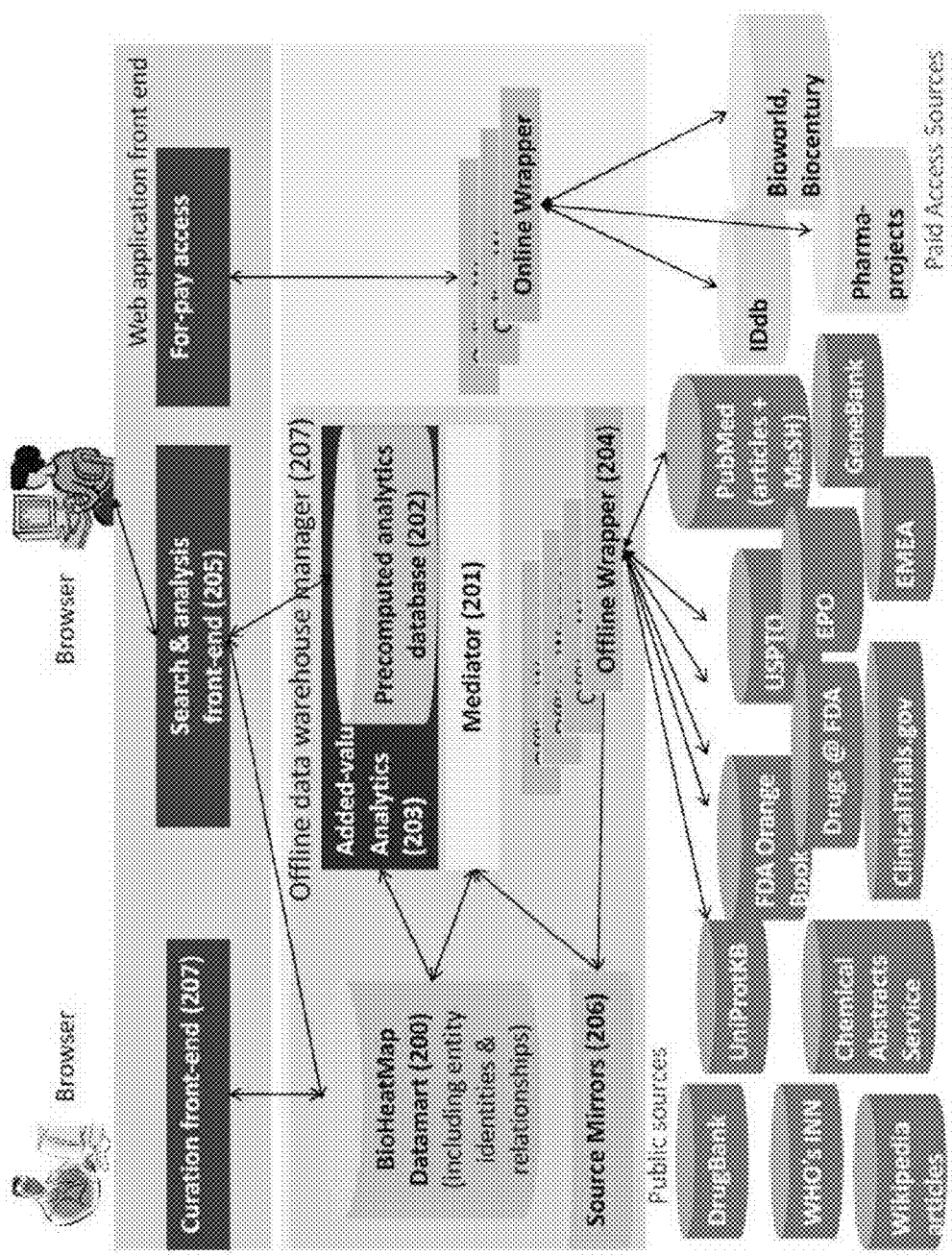
FIG. 2 shows the system Architecture of the preferred embodiment.
Figure 3:
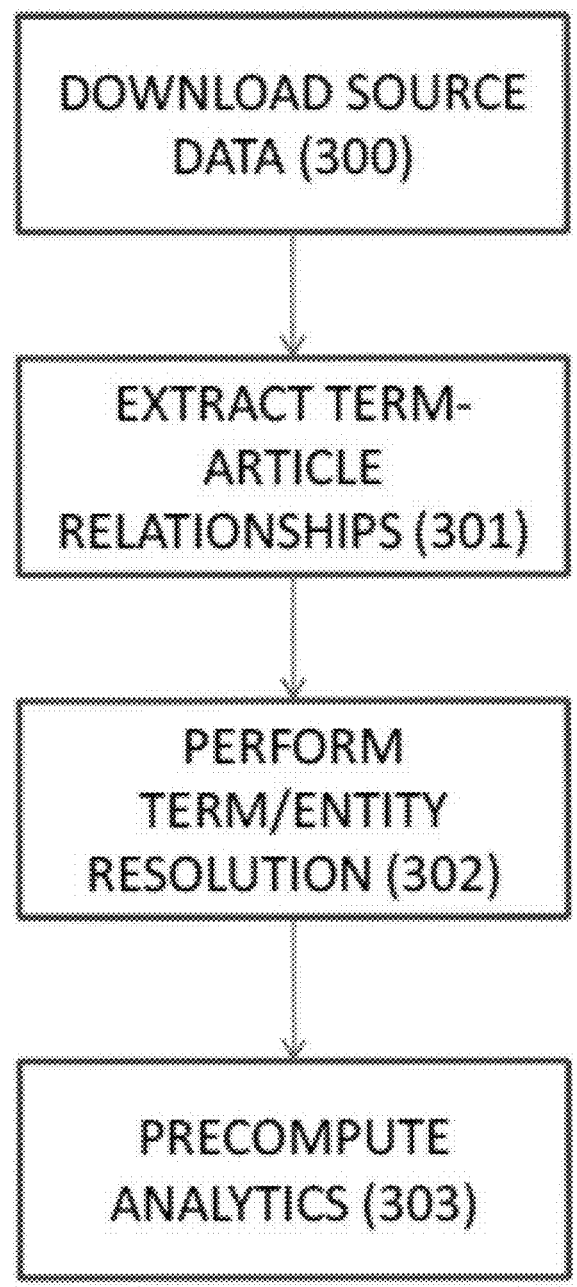
FIG. 3 shows the method of off-line data precomputation in the preferred embodiment.

In some embodiments, BioHeatMap (FIG. 2) includes an offline data warehouse manager and an online front end web application, which includes pages for search and analysis of the source data and pages for data curation. At a high level, the two modules operate as explained in FIGS. 3 and 4:

The offline data warehouse manager 207 has the system architecture shown in FIG. 2 and operates as explained in FIG. 3. It uses a mediator-wrapper architecture, with most of the integrated view being materialized. Every night (i.e., during off-peak hours) each offline wrapper 204 of the data warehouse manager 207 downloads the latest data from a corresponding source (Step 300), performs data extraction (301) and stores the result in the Source Mirrors database 206. While the maintenance of a mirror is not necessary, it may facilitate subsequent operations. For example, the offline wrappers that access the latest PubMed citations, using PubMed's web services, extract the author names, abstracts, etc. Each source mirror tracks the corresponding source's structure and terminology. The offline wrappers just transform various XML, HTML and textual formats used by the original sources into normalized SQL schemas. Therefore, the source mirrors of different sources are, in general, heterogeneous to each other. For example, the mirror that captures PubMed articles is using MeSH annotations while the mirror that captures FDA articles uses INN identifications. The offline wrappers are also responsible for collecting identifiers and metadata from the sources.

The mediator 201 accesses the source mirrors and outputs the BioHeatMap datamart 200, which is a set of SQL tables and accompanying files for the articles. The datamart uses its own internal term identities and preferred names for every substance, indication, etc, while it also maintains identity correspondence tables that indicate how the various terms used by sources correspond to the internal identities. For example, one substance record may indicate that there is a substance with internal identity 123 and preferred name "oxytocin", while a record of an identity correspondence table will indicate that internal substance 123 corresponds to the chemical identified as 50-56-6 by the Chemical Abstracts Service. Such correspondences have been resolved in 302. The automatically created identity correspondence tables may be edited and/or augmented by a human curator operating via the curation front-end 207.

The datamart also captures in tables the relationship of articles to substances, indications, molecular targets and more. This second important function of the mediator (Step 301) is the extraction of the ontology terms from the text of the articles and the establishment of article/term relationships in 301. For example, in BioHeatMap, substance and disease terms are extracted from the titles and abstracts of the citations. Notice that a term may be found in one of its many synonymous forms. Furthermore the mediator may employ smart parsing and stemming in order to spot certain terms. For example, it is appropriate to consider that a term is found regardless of whether it is plural or singular form was found. In some embodiments, it is determined that a relationship has been found between a term and an article if the mediator has deemed that such term appears in the article.

Both identity correspondences and relationships may be soft, in the sense that in the general case (1) they are not fully certain and (2) they are likely automatically produced, with a probability of error by the mediator.

While not necessary, it is advised that 301 precedes 302 because the association of articles with terms (i.e., entities) leads to better entity resolution. For example, there are generally multiple authors with the same name and, vice versa, the same author may appear under slightly different names. Knowing the association of each author with articles and the association of articles with other terms, the mediator disambiguate and resolves author entity instances. In particular, using the assumption that an author will typically work in the same area and topics, it is reasonable to cluster together instances of a name that appear in the same area but not instances that are thematically far apart.

Finally the added-value analytics component 203 of the offline data warehouse manager may precompute (303) various analytics and term correlations 202 that are too expensive to compute online.

Figure 4:
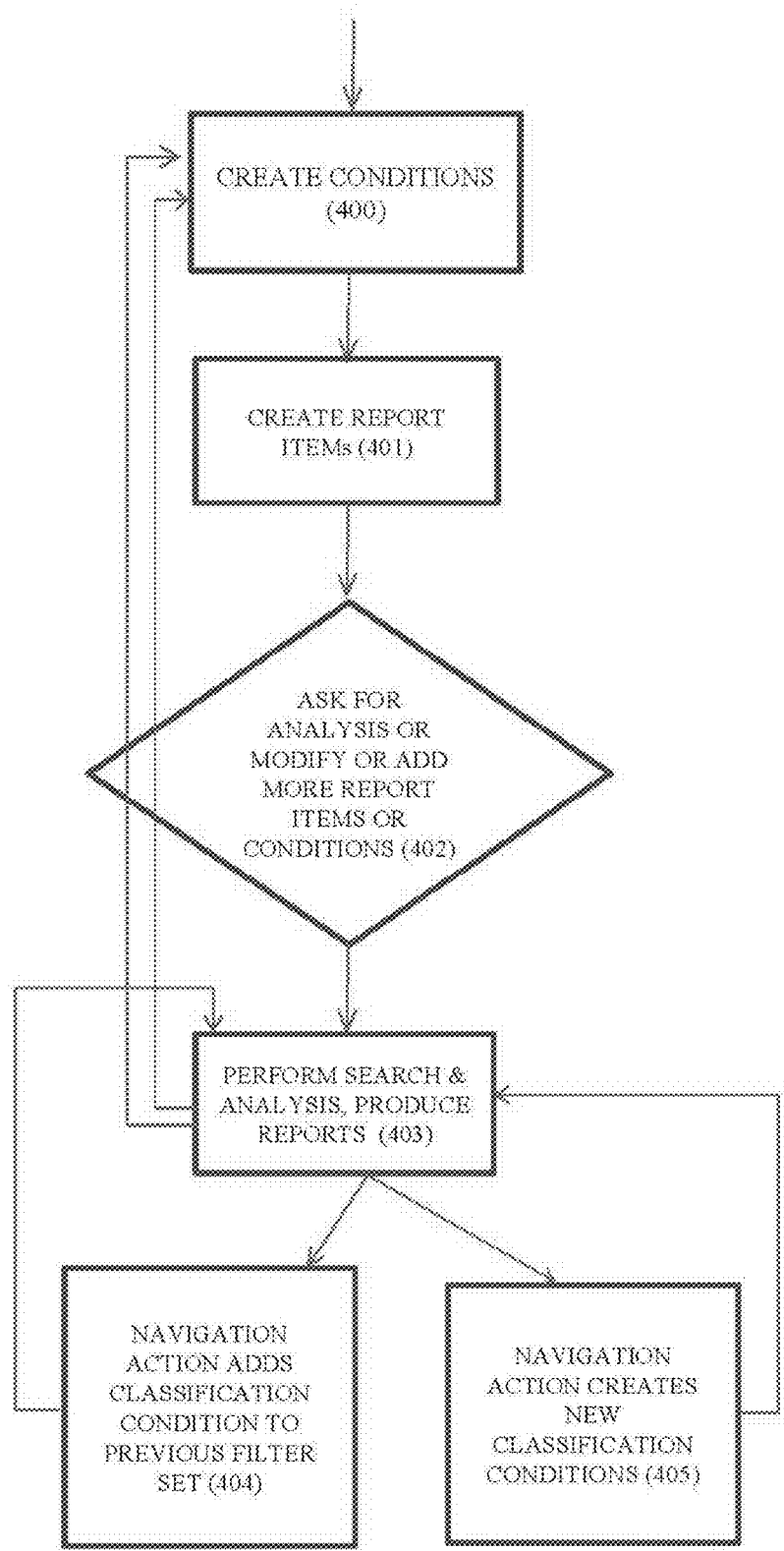
FIG. 4 shows the method of interaction in the preferred embodiment.

The datamart 200 and the precomputed analytics 202 are used by the browser-accessible search and analysis front end 205, whose operation is described in FIG. 4. Using 205, the user performs various search and analysis operations using BioHeatMap's interface that enables results involving both precomputed analytics 202 as well as results obtained by issuing queries that process the data of 200 and 202.

Figure 8:
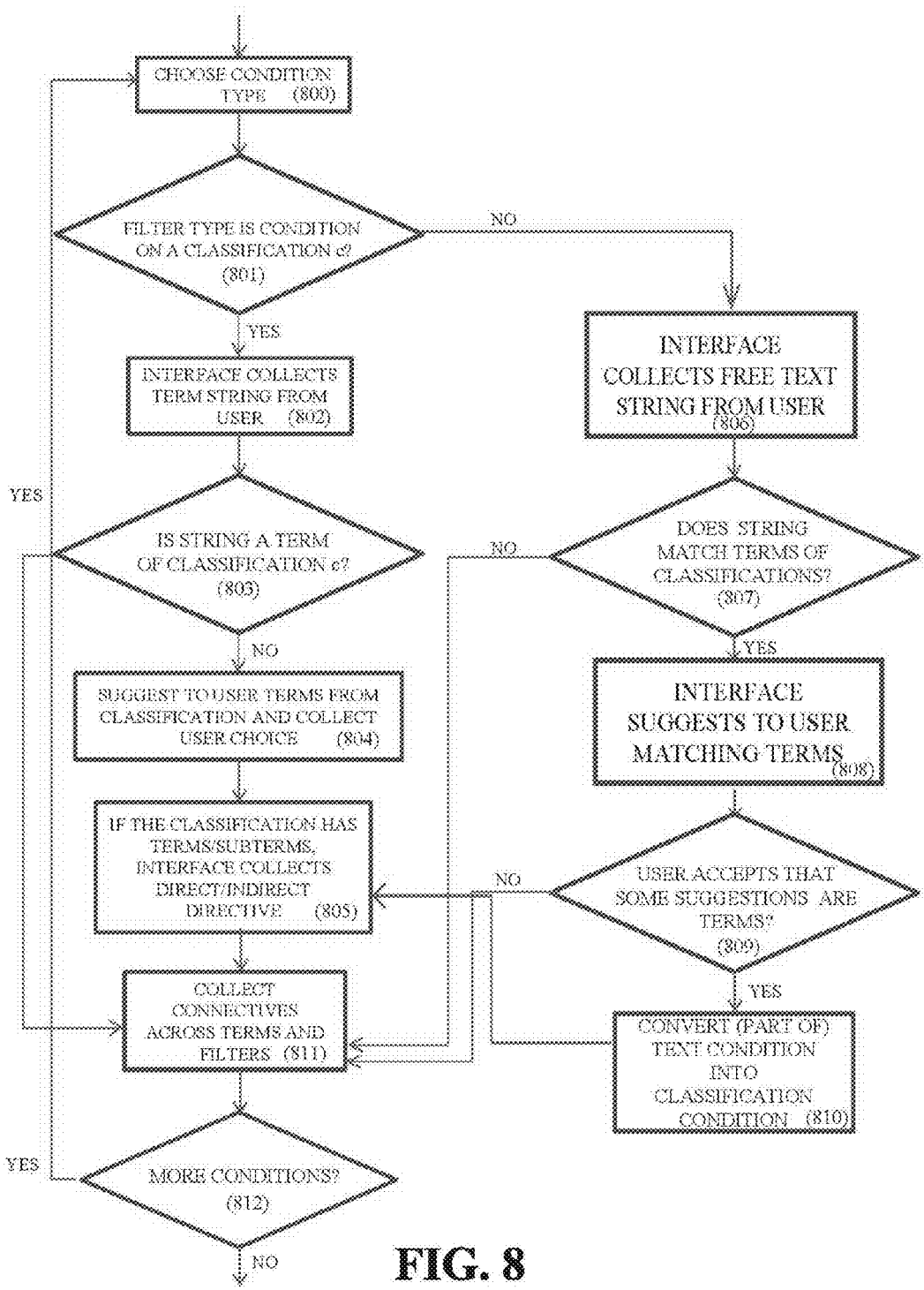
FIG. 8 is a flowchart depiction of a process of interaction towards formulating classification conditions.

In each step of the operation of 205, the user may create a condition in 400. FIG. 8 describes how the preferred embodiment enables the development of conditions. Depending on whether the user wants to build a text condition or a classification condition (choice in steps 800-801) the method proceed accordingly. For an example of classification condition, the user may specify that he wants articles that are associated with substance terms that are "vasopressin" or subterms thereof. In step 802 he provides a string that is a term of the classification or matches the term. In step 804 the method may suggest to the user terms that match the provided string and the user may choose among them. The suggestions come from the terms of 200. In step 805 the user specifies whether he is interested (or not) in documents that may not contain the exact term that he provided but may contain subterms and/or synonyms thereof. Finally in step 811 the user specifies how the multiple provided conditions logically connect with each other (eg, "AND", "OR", "NOT"). The step 804 allows the user to choose terms by any of the many synonyms thereof he may know. For example, the user may type "desmopressin"; the method will find that the name desmopressin corresponds to the term deamino arginine vasopressin. During the analysis phase (Step 404) any article that is related to deamino arginine vasopressin either directly or thru one of its many synonyms will qualify. The user may also build text conditions (step 806) while the method investigates in steps 807-809 whether a text condition should be converted to a classification condition (partially or totally) and if the user agrees it does so in step 810.

Figure 9:
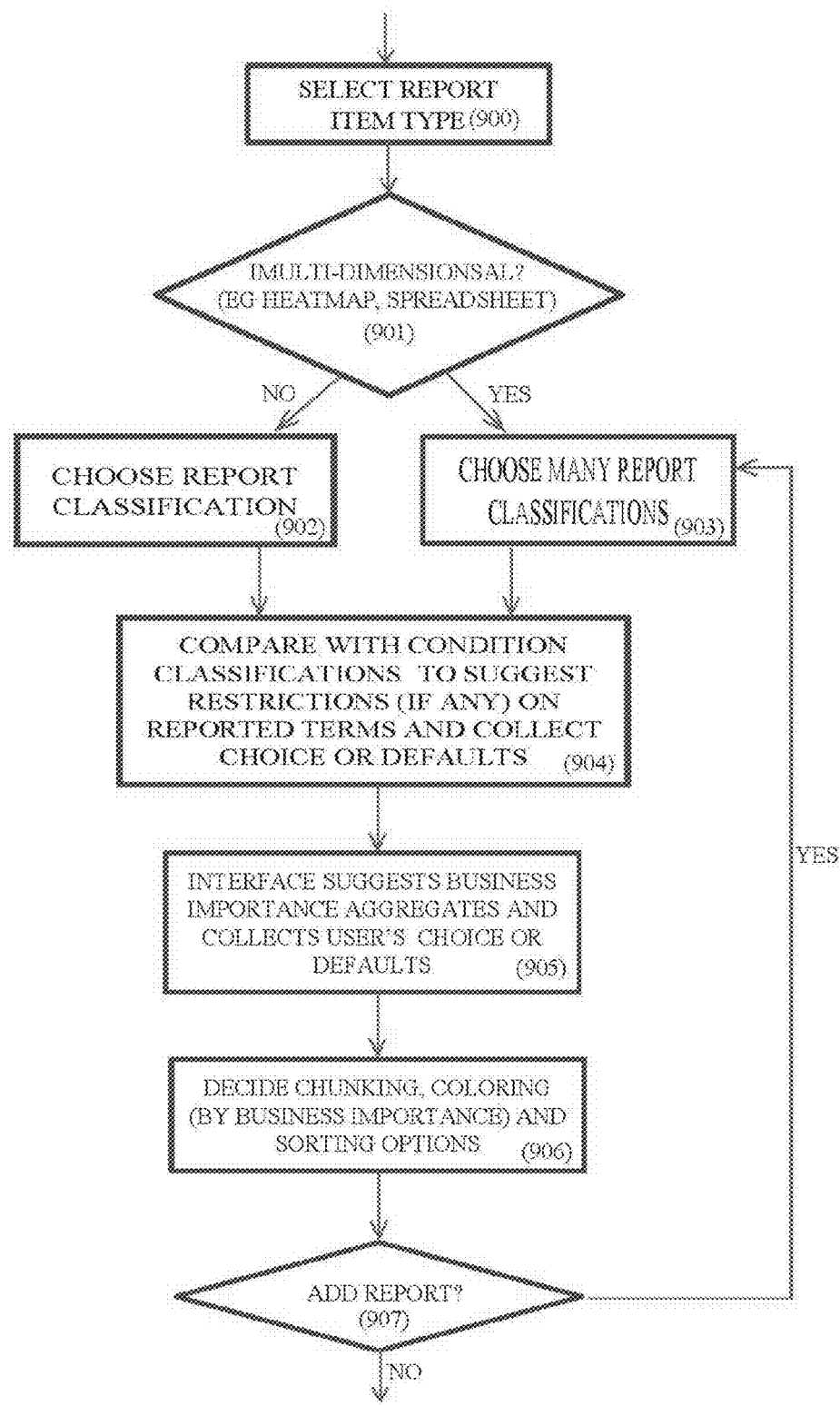
FIG. 9 shows the method of interaction towards formulating report classifications.

The user may also create report items 407, such as barcharts, time charts, tables, pie charts, spreadsheets and heatmaps. The details of creating reports are illustrated in FIG. 9. In BioHeatMap, Steps 902 and 903 allow a choice of dimensions such as "substance", "disease", "year", "journal" and more. Two dimensional report items require that two dimensions are specified. For example, the heatmap of FIG. 1 reports the two dimensions substance and disease. Given a set of filters (not shown in FIG. 1) the heatmap of FIG. 1 reports that there were, for example, 33 articles that met the filter conditions and are associated with Deamino Arginine Vasopressin and von Willebrand diseases. A subtle point (step 904) is whether a report classification that is also a condition classification should only display the terms mentioned explicitly in the condition, or their subterms also, or any term of such classification that is eventually related.

In the case of heatmaps, an extra chosen aspect is the choice of "heat" coloring. For example, if one of the dimensions is year, the heatmap can color the years that were busy with activity for a substance or disease with a more intense color, therefore providing a quick visual impression on whether a certain term becomes "hot" in the literature recently. In another example in FIG. 1, it is reported that there are 7 articles (that satisfy the filter conditions) that relate to the substance "lypressin" and to the disease "septic shock". Note that the color scheme conveys the importance of each cell. For example, a cell may be hotter because it corresponds to more articles, or more recent articles or more important articles, such as clinical trials and case reports.

Figure 6:
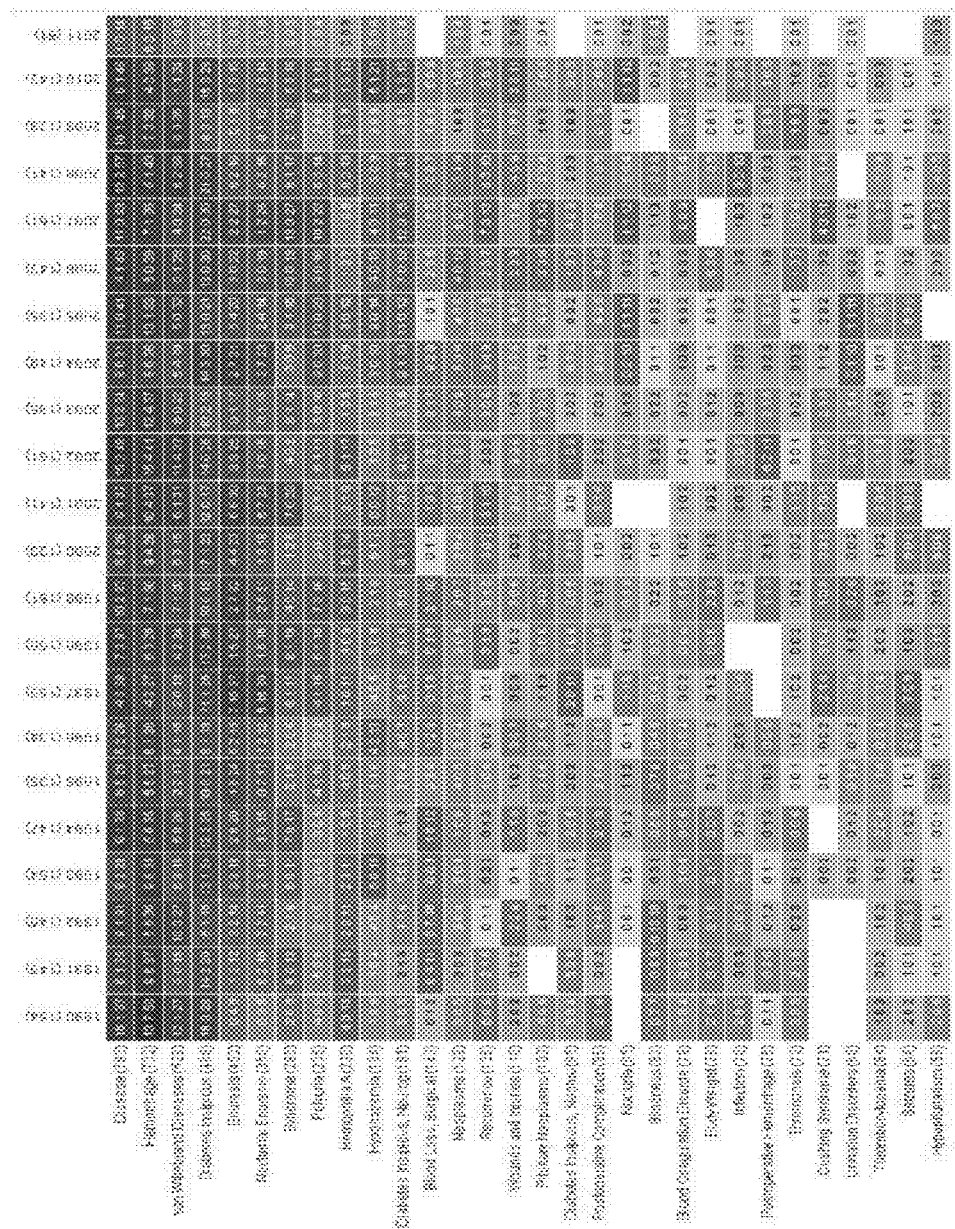
FIG. 6 shows a second instance of a heatmap analyzing literature across two dimensions, disease and year.

Note that the heatmap may display more than one metrics in each cell. For example, each cell in FIG. 6 shows numbers of case reports, clinical trials and of remaining articles. Importantly, some aggregate metrics may capture business importance and, in such case, they may be visualized by "heat colors" as opposed to plain numbers.

The user may choose (Step 403) to add more filters and report items, modify the existing ones, or proceed to ask for analysis to be performed (choice of Step 402, leading to analysis in 403).

The user may create a new report with just one or two clicks by utilizing the navigation features of the report items (Steps 404 and 405). For example, by clicking on the "lypressin" tag the user can be given options such as:

Show articles that satisfy the existing filters and are also associated with lypressin.

Show a comprehensive dossier that involves multiple report items about lypressin. For example, a BioHeatMap dossier about a substance consist of a heatmap of authors and years (that is, shows who published on what year about this topic), a plain author table of authors that have written about along with counts and chronology ranges of their articles, other substances that appear in lypressin articles, a table of journals where lypressin appears, a barchart or timechart summarizing activity on lypressin over the years, and so on.

Add a classification filter (condition) that the qualifying articles must also be associated with lypressin and run again the analysis.

Sort the heatmap according to the lypressin activity. That is, diseases that have the highest article counts on lypressin will appear towards the left of the disease dimension.

Similarly many options can appear upon clicking on a cell of the heatmap, except that clicking on a cell provides (with a single click) a context of two dimensions. For example, by clicking on the lypressin/septic shock cell, one may get options that change the report by adding filters that relate articles with both lypressin and septic shock.

The interface requires a number of coordinated innovations on the structure of the BioHeatMap datamart, called flexible snowflake and its use by the front end. One advantageous feature of the snowflake's classification is the use of terms/subterms. These innovations resolve challenges that broadly result from the mismatch between the type of data involved in conventional data cubes for sales and marketing versus the article-centered data that the BioHeatMap captures and analyzes. The former are numerically-oriented data (typically sales) that are classified in well-structured hierarchies (captured by the star and snowflake schema patterns) while BioHeatMap's classification of articles under substances, indications, etc. is characterized by flexibility and degrees of freedom that require a novel concept of data cube dimensions and expand beyond conventional roll-up, drill down and filtering paradigms.

Architecturally, the front end issues SQL queries to the datamart and visualizes their results using modern content-rich web components, such as a heatmap component.

The Added-Value Analytics module augments the BioHeatMap datamart with precomputed materialized views for analytics whose evaluation is too expensive to be done at run time.

Figure 5:
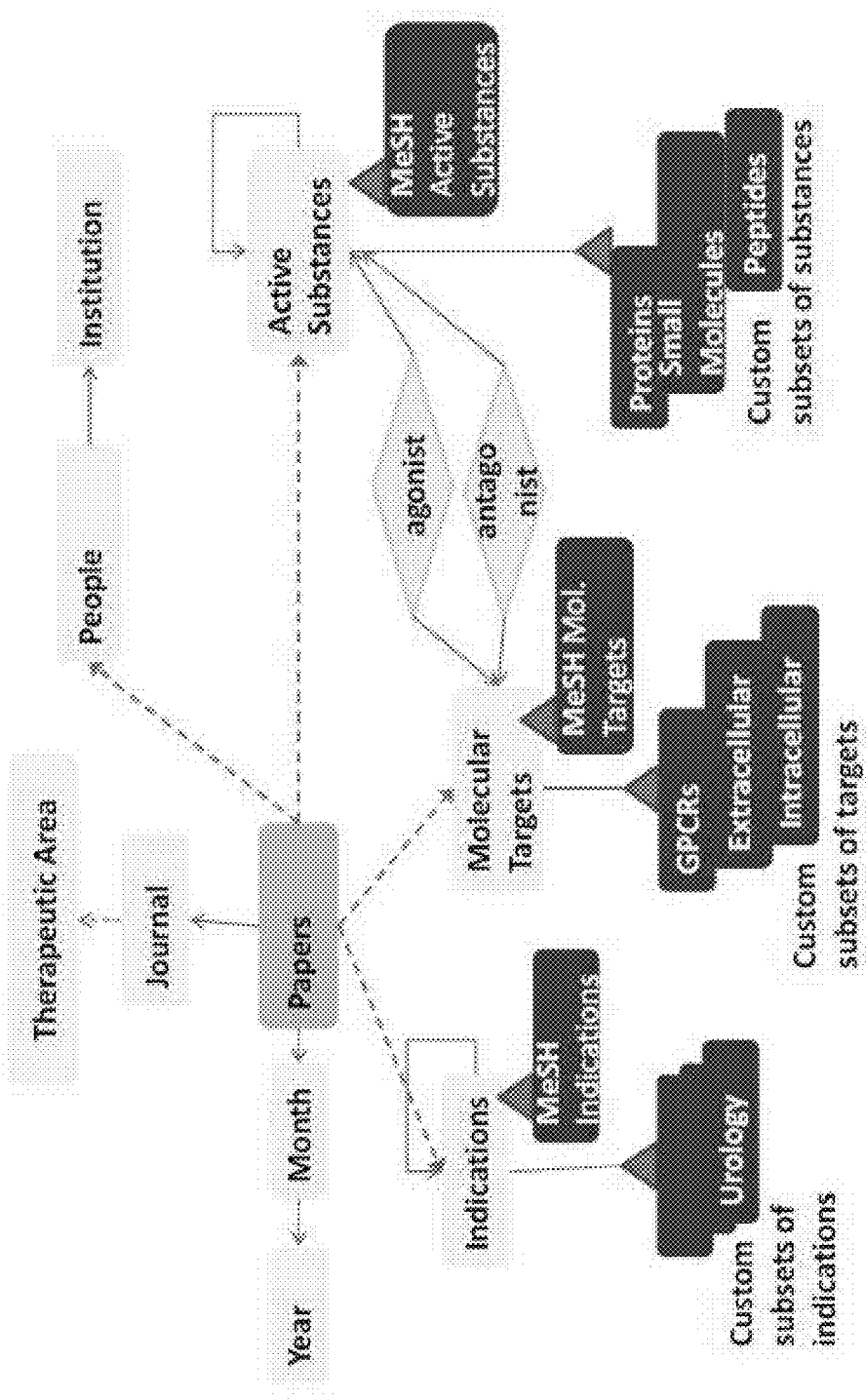
FIG. 5 shows the database schema in the preferred embodiment.

The BioHeatMap datamart's schema is shown in FIG. 5. Notice its teaching on relating literature (papers/articles) with ontology terms.

The "Article" table has one record for each article collected from the sources. The "Article" table is in effect the fact table of the data cube in the sense that the numerical measures displayed by the front end are weighed counts of articles that meet various conditions. An article is related to dimension (or classification) tables (e.g., indications, active substances, molecular targets, people), which are the tables depicted in light gray boxes in FIG. 5. In the spirit of data cube terminology, each record of a dimension table is called a dimension value. For example, the active substance "vasopressin" is a value in the dimension "Active Substances". Therefore the "Active Substances" dimension table contains a record with this value. A fact can be some information that is useful for search purpose. For example, a fact can be a document referring to a disease and a substance (for biomedical searches) or a sales receipt that refers to customers and products (for business searches), and so on.

Each relationship between articles and dimensions is indicated by an arrow and essentially classifies articles under the dimension values. Notice that unlike typical snowflake schemas the datamart also uses many-to-many classifications. In particular, articles are classified into dimensions using both:

many-to-one classifications: For example, each paper is related to exactly one a journal. The many-to-one classifications are indicated by arrows.

many-to-many classifications: For example, each article is related to possibly many indications. The many-to-many classifications are indicated by the thick dotted lines.

Each dimension's values may themselves be classified into other dimension values, as indicated by arrows such as the one that classifies journals into therapeutic areas. In an extension to conventional datacubes, some of the dimensions (notably, indication and active substance) are also classified into themselves, which is illustrated by arrows that start and end at the same dimension table. This extension is useful in describing indication and active substance values and is already used by PubMed's MeSH indications and substances. (MeSH substances and indications are a subset of all indications and substances, as indicated by the triangles in FIG. 5.) For example, in MeSH, an indication may be classified into a more general indication, which in turn may be classified into an even more general indication and so on. There is no standard on how deep this classification is. As an example data point, the indication "Crohn's disease" is classified into the broader indication "Inflammatory bowel disease", which also includes "Ulcerative colitis". Then "Inflammatory bowel disease" belongs to the even broader term "Gastroenteritis". Similarly the active substances are classified into themselves according to hierarchies of unknown depth.

We call flexible dimensions the ones that participate in many-to-many and self-classifications. We will correspondingly refer to BioHeatMap's snowflake as a flexible snowflake.

BioHeatMap's user interface, as described with respect to FIG. 4, provides pages that enable search and navigation along the flexible dimensions.

Querying the Datamart with the BioHeatMap Front-End

Figure 7:
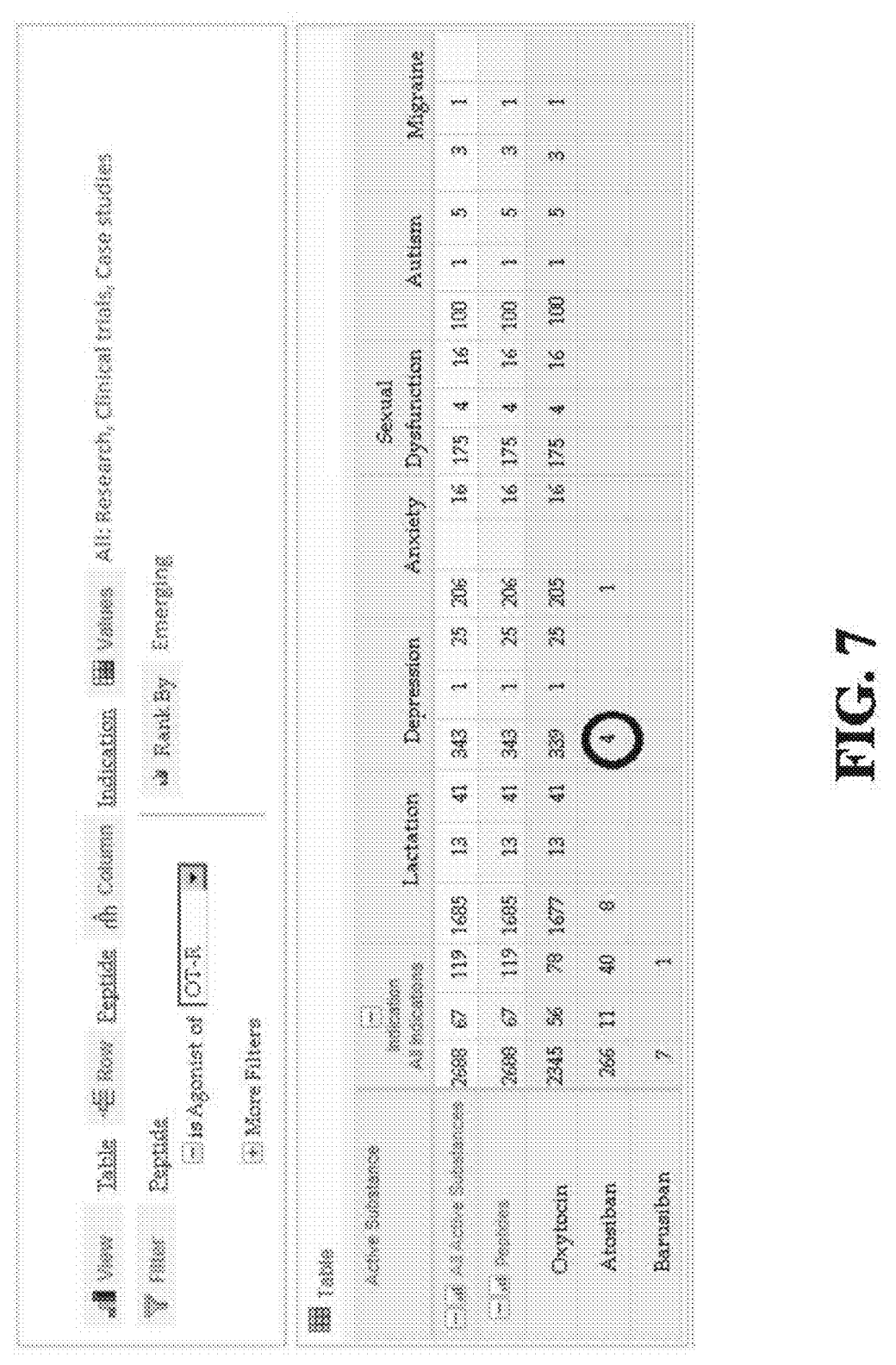

We illustrate an embodiment of the front end in FIG. 7 with a use case where the researcher inspects clinical indications associated with peptides that are oxytocin receptor (OT-R) agonists. As used in this document, an agonist is a substance that mimics the action of a naturally occurring substance. Methods related to the proposed front end functionalities are discussed.

The front end consists of four areas where the user chooses aspects of the reports he wants to see. The view area enables choosing the one or two dimensions that will be displayed and the particular visual format. In the running example the user has chosen the table format. He chose the rows to be peptides (that is a subset of substances) and the columns to be indications. Therefore each cell of the table corresponds to a peptide-indication connection. In the example, each cell contains (1) the number of research papers, (2) the number of case reports and (3) the number of clinical trials. The circled cell indicates that there are 4 research papers, no case studies and no clinical reports involving the substance "atosiban" and the indication "depression". More compact views are produced by choosing to show only research papers, or only case studies or only clinical trials.

The filter area allows the user to place conditions on both the reported dimension values and the reported articles. In general, each dimension is associated with a set of conditions that are applicable to it. For example, substances/peptides can be filtered by basic conditions "peptide is agonist of molecular target x", "peptide is classified under another peptide y", "peptide contains z", etc. Then the user combines basic conditions using either AND or OR connectives. In the example the user has placed a filter that the reported peptides are agonists or antagonists of the OT-R receptor.

Because the interface can express a very wide class of queries, the user may confuse queries whose differences are subtle. For example, a query that restricts the reported peptides to agonists of OT-R is different from a query that restricts the reported articles to those that involve peptides that are agonists of OT-R. The latter query will lead to a report where a row may be a peptide x that is not an agonist of OT-R. Such a row will appear because there are articles that involve both x and an agonist of OT-R. An online guide pops up to hint subtleties, such as the one discussed above, to first time users.

With just two clicks, the user can drill down to investigate more details, roll up to have a higher level summary view or pivot to another dimension. Such actions are called navigations and their effect has also been described in FIG. 4. For example, by clicking on the column header "depression" the user is presented options to "view 'depression' articles in barchart format", "view 'depression' articles by year", "view all papers" and many more. Notice that the net effect of a navigation can also be achieved by changing choices in the view and filter areas. For example, clicking on "view 'depression' articles by year" is equivalent to creating a filter condition "disease='depression'" and changing the column dimension to "year". However, the user experience is superior by enabling the same with navigations, which require just two clicks.

Features "Hot" Emerging Literature as a Case of Aggregate of Business Importance FIG. 7 shows the numbers of articles corresponding to peptide/indication pairs. However, the total number of articles is often not a good enough metric for how important (hot) a connection is. For example, a large but decelerating literature volume on a certain connection is typically a bad sign since it often relates to a long ago studied and developed connection. In contrast, a recent and accelerating, even if low, volume of recent papers provides promising unexplored ideas.

BioHeatMap's rank & heat area solves the problem by enabling the researcher to customize the ranking metrics (possibly making them independent from the absolute numbers of papers) and highlight with heat visualization as in FIG. 7. For example, the user may choose the "Emerging Clinical" ranking option. In response, BioHeatMap prompts the user to provide the time period that corresponds to "recent" by choosing between "last week", "last month", "last quarter" or a custom period.

Information overload happens when filters are absent or not sufficiently selective. For example, the table that reports all peptide-indication connections is very large. While it has overview value for a student or a novice that learns about peptides, it has questionable value for a professional peptide researcher in a peptide-focused pharmaceutical, such as Ferring. Even for the novice, it is too large to overview. The front end will employ a list of summarization suggestions (prescribed by the front-end's administrator) in such cases. For example, the front end will suggest displaying therapeutic areas (instead of indications), when the listed indications exceed an administrator-provided threshold, such as 100 indications.

Customized Perspectives of Flexible Dimensions

An often deployed feature in corporate business intelligence data warehouses and data cubes is customized perspectives of the company's data to analysts with particular interests. Customized perspectives are even more important for BioHeatMap since different companies and researchers have different interests and perspectives on the biomedical literature. We discuss below the nature of the different perspectives, some of which are very particular to the biomedical literature, and propose mechanisms for accommodating them in the BioHeatMap datamart.

Focus Area:

Generally, a company or an individual researcher may obtain the ability to create custom subsets of interest of the flexible dimensions. For example, Ferring is interested in peptides (which is a subset of active substances) and their application to indications in urology, obstetrics/gynecology, fertility and gastroenterology. Subsets are indicated in FIG. 5 as the black boxes, relating to the parent dimension via triangles.

Perspective on Granularity:

Researchers at different stages of the discovery process care about different levels of granularity in the flexible dimensions' hierarchies. For example, an executive may not care initially about the connections of particular active substances classified as vasopressins (e.g., arginine, lypressin, etc). He may prefer to only consider vasopressins cumulatively, as a single substance. In contrast, the biochemist needs to know the exact vasopressin variant (e.g., arginine) involved. In summary, the two researchers look in the same area but at different levels of granularity.

Precomputations

Many of the queries issued by the front end will be too slow (>5 s) for online analysis if they are evaluated directly on the tables of the BioHeatMap datamart. The Added-value Analytics module of FIG. 2 will provide the requisite performance boost by precomputing various data (needed by the queries) and materializing them on disk-resident tables. Then the front end's queries will utilize such precomputed materialized tables and therefore avoid performing the full computation from scratch.

An alternate approach, which can also be employed, is avoiding precomputation and materialization by utilizing novel Massive Parallel Processing (MPP) architectures. In particular, many recent startups (eg, AsterData) displace conventional corporate OLAP architectures by selling infrastructure that speeds up queries by utilizing the power of many CPUs working in parallel to produce the query result. In such cases the literature analysis need not use precomputation preferred method utilizes dynamic query writing, whereas it creates on the fly a query that performs the analysis.

It will be appreciated that various embodiments for interactively analyzing a set of documents (i.e., a literature) utilizing an ontology are disclosed. In a first embodiment, the method accesses the set of documents and the ontology, which includes terms organized in one or more classifications, including the possibility that (in at least one of the classifications) terms may be classified as subterms of other terms. The system enables the user to place queries via a user interface that utilizes the ontology. Unlike, the prior art in document search where the system simply returns a set of documents, the system produces query answers that consist of multiple aggregate measures that indicate relationships between terms of the ontology and, therefore, assist the user in discovering knowledge from the literature. In one embodiment the system has precomputed and stored selected aggregate measures in a database in order to face the computational challenge posed by having to produce multiple aggregate measures within response times acceptable for interactive analysis. In particular, upon receiving the user request from the browser, the system accelerates processing by using the precomputed aggregate measures. The described technique enables the efficient interactive analysis of over 20,000,000 biomedical articles.

Figure 10:
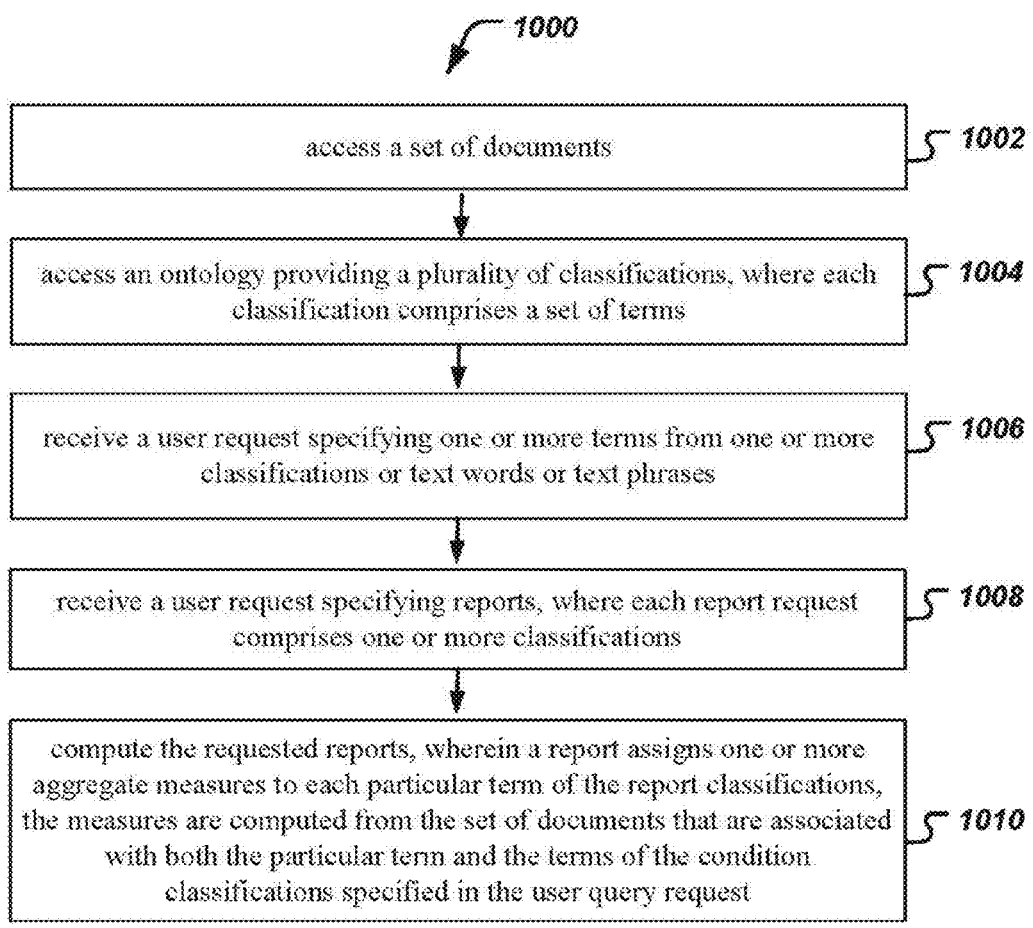
FIG. 10 is a flowchart representation of a process of providing search results to a user.

FIG. 10 is a flowchart representation of a process of providing search results to a user. At 1002, a set of documents are accessed. At 1004, an ontology providing a plurality of classifications is accessed, wherein each classification comprises a set of terms. At 1006, a user request specifying one or more terms from one or more classifications or text words or text phrases is received. At 1008, a user request specifying a report is reached. Each report request comprises one or more classifications. At 1010, the requested report is computed, wherein a report assigns one or more aggregate measures to each particular term of the report classifications, the measures are computed from the set of documents that are associated with both the particular term and the terms of the condition classifications specified in the user query request.

Figure 11:
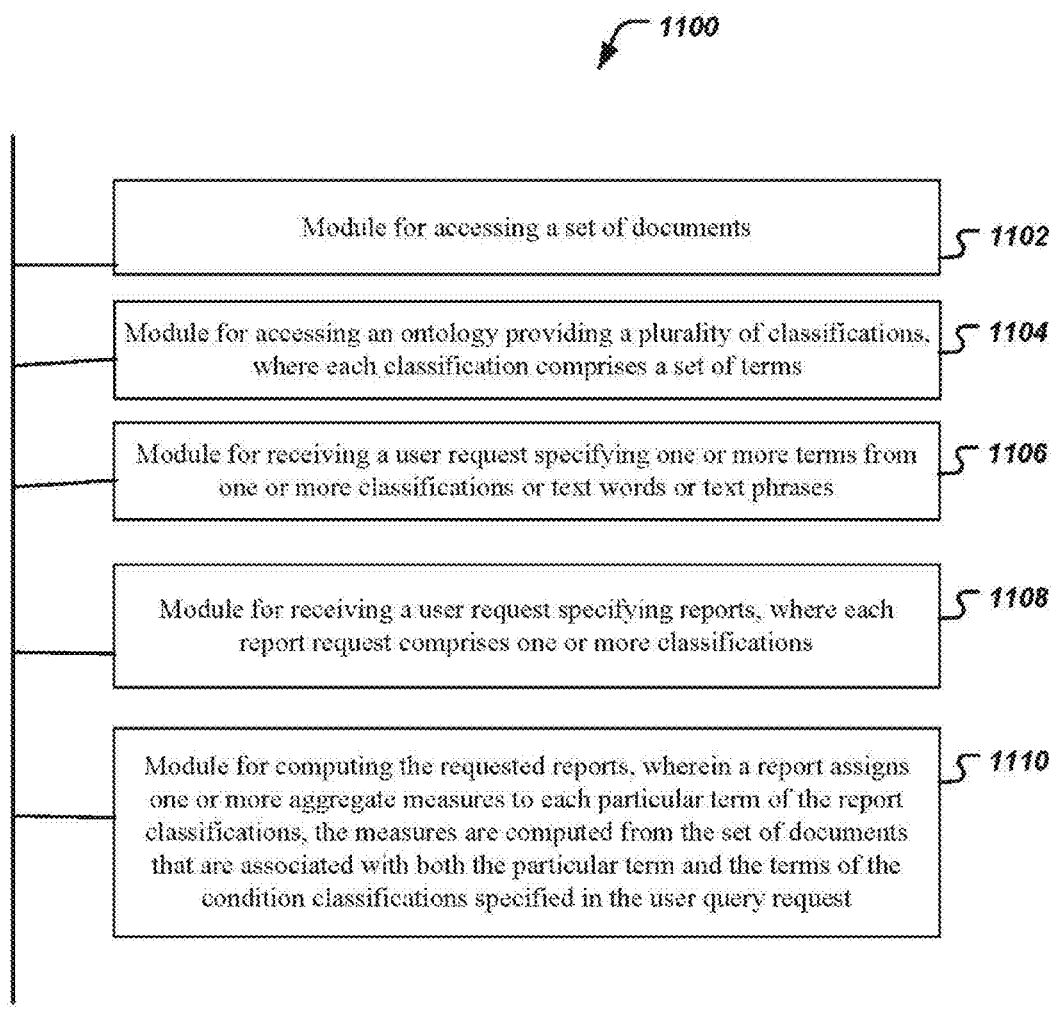
FIG. 11 is a block diagram representation of an apparatus for providing search results to a user.

FIG. 11 is a block diagram representation of an apparatus 1100 for providing search results to a user. The module 1102 is for accessing a set of documents. The module 1104 is for accessing an ontology providing a plurality of classifications, where each classification comprises a set of terms. The module 1106 is for receiving a user request specifying one or more terms from one or more classifications or text words or text phrases. The module 1110 is for receiving a user request specifying reports, where each report request comprises one or more classifications. The module 1112 is for computing the requested reports, wherein a report assigns one or more aggregate measures to each particular term of the report classifications, the measures are computed from the set of documents that are associated with both the particular term and the terms of the condition classifications specified in the user query request.

Figure 12:
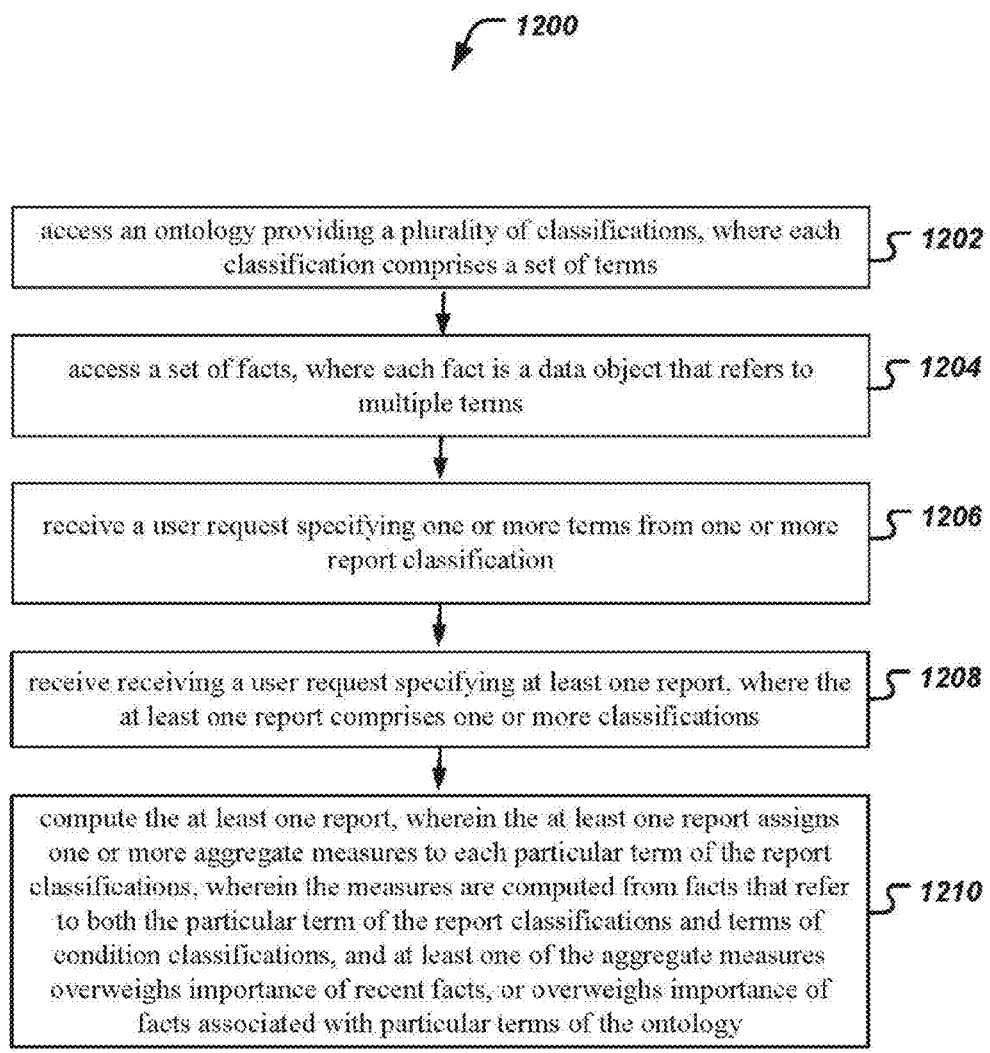
FIG. 12 is a flowchart representation of a computer implemented method of computing requested reports.

FIG. 12 is a flowchart representation of a computer implemented method 1200 of computing requested reports. At 1202, an ontology providing a plurality of classifications, where each classification comprises a set of terms is accessed. At 1204, a set of facts, where each fact is a data object that refers to multiple terms, are accessed. At 1206, a user request specifying one or more terms from one or more report classifications is received. At 1208, a user request specifying at least one report, where the at least one report comprises one or more classifications is received. The user request received at 1206 and 1208 may be the same or may be two different requests. At 1210, the at least one report is computed, wherein the at least one report assigns one or more aggregate measures to each particular term of the report classifications, wherein the measures are computed from facts that refer to both the particular term of the report classifications and terms of condition classifications, and at least one of the aggregate measures overweighs importance of recent facts, or overweighs importance of facts associated with particular terms of the ontology.

Figure 13:
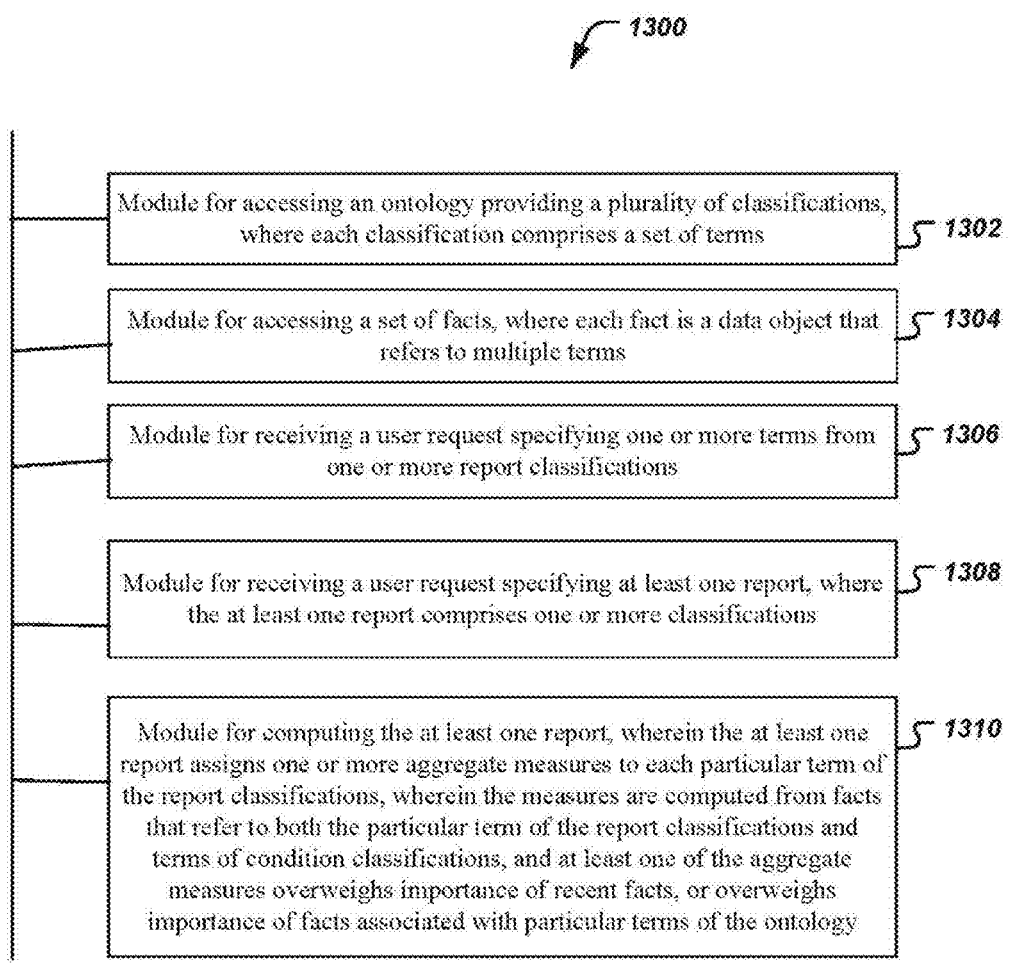
FIG. 13 is a block diagram representation of a report generation apparatus.

FIG. 13 is a block diagram representation of a report generation apparatus 1300. The module 1302 is for accessing an ontology providing a plurality of classifications, where each classification comprises a set of terms. The module 1304 is for accessing a set of facts, where each fact is a data object that refers to multiple terms. The module 1306 is for receiving a user request specifying one or more terms from one or more report classifications. The module 1308 is for receiving a user request specifying at least one report, where the at least one report comprises one or more classifications. The module 1310 is for computing the at least one report, wherein the at least one report assigns one or more aggregate measures to each particular term of the report classifications, wherein the measures are computed from facts that refer to both the particular term of the report classifications and terms of condition classifications, and at least one of the aggregate measures overweighs importance of recent facts, or overweighs importance of facts associated with particular terms of the ontology.

The search and presentation techniques, according to various aspect, can be described as below. Numbering is provided only for convenience. The examples provided below are illustrative and do not limit the subject technology.

Clause 1. A method, implementable on a computer, comprising:
 (a) accessing a set of documents;
 (b) accessing an ontology providing a plurality of classifications, where each classification comprises;
  (i) a set of terms;
  (ii) optionally, a list of synonyms for each term;
  (iii) optionally, a term/subterm relationship between terms of the same classification;
  (iv) optionally, associations between terms of different classifications;
 (c) receiving a user request (called the user query request) specifying;
  (i) one or more terms from one or more classifications (called condition classifications), or
  (ii) text words, or
  (iii) text phrases, or
  (iv) or combinations of the (i), (ii) and (iii).
 (d) receiving a user request (called the user report request) specifying reports, where each report request comprises
  (i) one or more classifications (called report classifications)
 (e) computing the requested reports, whereas a report assigns one or more aggregate measures to each particular term (or combination of terms) of the report classifications; the measures are computed from the set of documents that are associated with both the particular term (or combination of terms) and the terms of the condition classifications specified in the user query request.

Clause 2. The method of Clause 1, where at least one report involves at least two report classifications.

Clause 3. The method of Clause 2, where a report involving two report classifications is visualized by a 2-dimensional visualization.

Clause 4. The method of Clause 3 where the visualization is a 2-dimensional table.

Clause 5. The method of Clause 4 where the visualization is a 2-dimensional heatmap.

Clause 6. The method of Claim 1, where new report classifications and condition classifications are set by a navigation action initiated from a displayed report.

Clause 7. The method of Clause 1, where the ontology provides a list of synonyms for terms of at least one classification.

Clause 8. The method of Clause 1, where the ontology provides term/subterm relationships for terms of at least one classification.

Clause 9. The method of Clause 1, where the ontology provides associations between terms of different classifications.

Clause 10. The method of Clause 1, where the ontology is extracted from Internet-based sources.

Clause 11. The method of Clause 1, where the user can provide additional ontology terms or classifications via a user interface.

Clause 12. The method of Clause 2, where a user can provide synonyms via a user interface.

Clause 13. The method of Clause 8, where a user can provide term/subterm relationships via a user interface.

Clause 14. The method of Clause 9, where a user can provide associations between terms of different classifications via a user interface.

Clause 15. The user report request of Clause 1 further specifying whether the reported terms will be
  any term of the report classifications, or
  only the specified terms of the condition classifications, or
  the specified terms of the condition classifications and the subterms thereof Clause 16. The method of Clause 1 whereas the aggregate measures include at least one aggregate (called the business importance aggregate) that determines the business importance of a set of documents.

Clause 17. The method of Clause 16, whereas the documents pertain to biomedical discoveries and/or research and the business importance aggregate assigns higher measure to a report classification term when such term is associated with specific types of documents, such as case reports and clinical studies.

Clause 18. The method of Clause 16, whereas the business importance aggregate assigns higher rank to a report classification term when such term is associated with many recent documents.

Clause 19. The method of Clause 16, whereas the business importance aggregate assigns higher rank to a report classification term according to how the number of recent documents associated to the term exceeds the past average of the number documents associated to the term.

Clause 20. The method of Clause 16, whereas the computation of the business importance aggregate utilizes the relevance of each result document to the terms.

Clause 21. The method of Clause 1, whereas a user interface assists the user in identifying terms of the ontology.

Clause 22. The method of Clause 21, whereas the user interface identifies that words and phrases provided by the user in the user query request correspond to ontology terms and explains to the user the correspondence.

Clause 23. The method of Clause 1, where at least one condition classification involves a term/subterm relationship.

Clause 24. The method of Clause 23, where the user query request distinguishes whether:
  the qualified documents have to be directly associated with the provided terms of the condition classification; and
  the qualified documents may be associated either directly with the provided terms of the condition classifications or indirectly, via the term/subterm relationship of the condition classification Clause 25. The method of Clause 1, where the method computes in advance the associations of terms and documents and stores such associations in a database.

Clause 26. The method of Clause 25, where discovering an association between a term and document is based on detecting the presence of any of the synonyms or subterms of the term in the document.

Clause 27. The method of Clause 25, where aggregate measures have been precomputed in the database and the computation of the requested reports utilizes such precomputed aggregate measures.

Clause 28. The method of Clause 1, where a report classification is customized according to the business perspective of the user.

Clause 29. The method of Clause 28, where the customization comprises choosing a subset of a report classification's terms.

Clause 30. The method of Clause 28, where the customization comprises simplifying the term/subterm relationship.

Clause 31. A method comprising:
  accessing a set of facts,
  accessing an ontology providing a plurality of classifications, where each classification comprises a set of terms and the facts are associated to the terms.
  receiving a user request (called the user query request) specifying one or more terms from one or more classifications (called condition classifications),
  receiving a user request (called the user report request) specifying one or more reports, where each report comprises one or more classifications (called report classifications)
  computing the requested reports, whereas a report assigns one or more aggregate measures to each particular term (or combination of terms) of the report classifications; the measures are computed from the facts that are associated with both the particular term (or combination of terms) of the report classifications and the terms of the condition classifications; and at least one of the aggregate measures (called the business importance measure)
  overweighs the importance of recent facts, or
  overweighs the importance of facts associated with particular terms of the ontology.

Clause 32. The method of Clause 31, whereas at least one report visualizes the business importance of each term (or of each combination of terms).

Clause 33. The method of Clause 32, whereas the visualization is provided in the form of a heatmap.

Clause 34. The method of Clause 31, whereas the reported terms are ranked according to their business importance measures.

Clause 35. The method of Clause 31, whereas the facts are documents.

Clause 36. A computer-implemented method, comprising:
  receiving a user query request comprising condition classifications or text words or text phrases;
  receiving a user report request comprising report classification information that includes a request term;
  accessing an ontology providing a plurality of classifications, where each classification comprises a set of terms;
  accessing, using the ontology, a set of document associated with the report classification information;
  computing an aggregate measure of the request term based on a relationship between the request term and the set of documents;
  generating a requested report based on the aggregate measure of the request term;
  and
  presenting the requested report Clause 37. A method of presenting search results to a user, the method comprising receiving a request comprising a search term and a ranking metric;

generating a search report for the search term using the ranking metric;

presenting the search report as a two dimensional color map along a first axis corresponding to the ranking metric and a second axis corresponding to a time period of a search result included in the search, wherein colors used in the color map provide a visual indication to a user of relevancy of search results in the search report according to the ranking metric.

Clause 38. The method recited in clause 37, wherein the color map uses color temperatures so that a color temperature assigned to a search result is proportional to its relevancy based on the ranking metric.

The disclosed and other embodiments and the functional operations described in this document can be implemented in digital electronic circuitry, or in computer software, firmware, or hardware, including the structures disclosed in this document and their structural equivalents, or in combinations of one or more of them. The disclosed and other embodiments can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

What is claimed is what is described and illustrated, including:

1. A computer-implemented method of providing search results, the method comprising:

accessing an ontology providing a plurality of classifications, where each classification comprises a set of terms;

accessing a set of documents comprising at least two documents, wherein each document in the set is associated with one or more classification from the plurality of classifications and there is at least one classification that relates at least one document to multiple terms of the at least one classification;

receiving a user query request specifying one or more condition terms from one or more classifications or text words or text phrases;

receiving a user request specifying reports, where each user request comprises one or more classifications representing one or more dimensions of visualization of the reports; and computing the requested reports by assigning one or more aggregate measures to each combination of a particular report term from each one of the report classifications, wherein at least one aggregate measure is computed from a set of documents that are associated with every combination of the particular report terms and also relates to the condition terms or text words or text phrases in the user query request, wherein at least one aggregate measure overweighs the importance of recent facts in a fact table, or overweighs the importance of facts associated with the particular terms of the ontology.

2. The method of claim 1, where at least one report involves at least two report classifications and a report assigns one or more aggregate measures to each particular combination of terms of the report classifications, the measures are computed from the set of documents that are associated with both the particular terms and the terms of the condition classifications specified in the user query request.

3. The method of claim 2, where a report involving two report classifications is visualized by a 2-dimensional visualization.

4. The method of claim 3 where the visualization is a 2-dimensional table.

5. The method of claim 3 where the visualization is a 2-dimensional heatmap that uses a color scheme that conveys importance of each cell of the 2-dimensional visualization.

6. The method of claim 2, where a user can provide synonyms via a user interface.

7. The method of claim 1, where new report classifications and condition classifications are set by a navigation action initiated from a displayed report.

8. The method of claim 1, where the ontology is extracted from Internet-based sources.

9. The method of claim 1, where the user can provide additional ontology terms or classifications via a user interface.

10. An apparatus, comprising:
a memory that stores program instructions; and
a processor that reads the program instructions and implements a method of providing search results to a user, the method comprising:
accessing an ontology providing a plurality of classifications, where each classification comprises a set of terms;
accessing a fact table comprising at least two facts, wherein each fact comprises a document and each fact is associated with one or more classification from the plurality of classifications and there is at least one classification that relates at least one fact to multiple terms of the at least one classification;
receiving a user query request specifying one or more condition terms from one or more classifications or text words or text phrases;
receiving a user request specifying reports, where each user request comprises one or more classifications representing one or more dimensions of visualization of the reports; and
computing the requested reports by assigning one or more aggregate measures to each combination of a particular report term from each one of the report classifications, wherein at least one aggregate measure is computed from a set of qualifying facts that are associated with every combination of the particular report terms of the ontology, and also relates to the condition terms or text words or text phrases in the user query request.

11. The apparatus of claim 10, where the ontology provides a list of synonyms for terms of at least one classification.

12. The apparatus of claim 10, where the ontology provides term/subterm relationships for terms of at least one classification.

13. The apparatus of claim 10, where the ontology provides associations between terms of different classifications.

14. The apparatus of claim 10, where the ontology is extracted from Internet-based sources.

15. The apparatus of claim 10, where the user can provide additional ontology terms or classifications via a user interface.

16. The apparatus of claim 10, wherein a user interface assists the user in identifying terms of the ontology.

17. The apparatus of claim 16, wherein the user interface identifies that words and phrases provided by the user in the user query request correspond to ontology terms and explains to the user the correspondence.

18. The apparatus of claim 10, where at least one condition classification involves a term/subterm relationship.

19. A computer-implemented method of computing requested reports, comprising:
accessing an ontology providing a plurality of classifications, where each classification comprises a set of terms;
accessing a set of documents comprising at least two documents, where each document is associated with one or more classifications including a classification that relates at least one document to multiple terms of the classification;
receiving a user request specifying one or more condition terms from one or more classifications or text words or text phrases;
receiving a user request specifying at least one report, where the at least one report comprises one or more classifications representing one or more dimensions of visualization of the reports; and
computing the requested reports by assigning one or more aggregate measures to each combination of a particular report term from each one of the report classifications, wherein at least one aggregate measure is computed from a set of documents that are associated with every combination of the particular report terms and also relates to the condition terms or text words or text phrases in the user query request,
wherein at least one aggregate measure overweighs the importance of recent facts in a fact table, or overweighs the importance of facts associated with the particular terms of the ontology.

20. The method of claim 19, wherein at least one report visualizes business importance of each term.

* * * * *